US010393723B2

(12) United States Patent
Watanasiri et al.

(10) Patent No.: US 10,393,723 B2
(45) Date of Patent: Aug. 27, 2019

(54) METHOD TO REPRESENT METAL CONTENT IN CRUDE OILS, REACTOR FEEDSTOCKS, AND REACTOR PRODUCTS

(71) Applicant: Aspen Technology, Inc., Bedford, MA (US)

(72) Inventors: Suphat Watanasiri, Sharon, MA (US); Shu Wang, Acton, MA (US); Lili Yu, Shanghai (CN)

(73) Assignee: ASPEN TECHNOLOGY, INC., Bedford, MA (US)

(*) Notice: Subject to any disclaimer, the term of this patent is extended or adjusted under 35 U.S.C. 154(b) by 548 days.

(21) Appl. No.: 15/047,347

(22) Filed: Feb. 18, 2016

(65) Prior Publication Data

US 2016/0162664 A1 Jun. 9, 2016

Related U.S. Application Data

(63) Continuation-in-part of application No. 13/740,095, filed on Jan. 11, 2013, now Pat. No. 9,934,367.

(60) Provisional application No. 61/644,792, filed on May 9, 2012, provisional application No. 61/586,268, filed on Jan. 13, 2012, provisional application No. 62/155,791, filed on May 1, 2015.

(51) Int. Cl.
*G01N 33/28* (2006.01)
*G06Q 50/02* (2012.01)
*G16C 20/30* (2019.01)

(52) U.S. Cl.
CPC ......... *G01N 33/2823* (2013.01); *G06Q 50/02* (2013.01); *G16C 20/30* (2019.02)

(58) Field of Classification Search
None
See application file for complete search history.

(56) References Cited

U.S. PATENT DOCUMENTS

| 5,223,714 | A | 6/1993 | Maggard |
| 5,699,269 | A | 12/1997 | Ashe et al. |
| 5,808,180 | A | 9/1998 | Roussis et al. |
| 6,662,116 | B2 | 12/2003 | Brown |
| 8,546,146 | B2 | 10/2013 | Butler et al. |
| 8,916,722 | B2* | 12/2014 | Yaghi ............ C07F 3/003 556/132 |
| 9,625,439 | B2* | 4/2017 | Saeger ............ G01N 33/2835 |
| 9,934,367 | B2* | 4/2018 | Chen ............... G01N 33/2823 |
| 2003/0195708 | A1 | 10/2003 | Brown |
| 2008/0248967 | A1 | 10/2008 | Butler et al. |
| 2009/0105966 | A1 | 4/2009 | Brown et al. |
| 2012/0153139 | A1* | 6/2012 | Qian .............. G01N 33/2835 250/282 |
| 2013/0185044 | A1 | 7/2013 | Chen et al. |
| 2013/0325362 | A1 | 12/2013 | Saeger et al. |
| 2015/0106028 | A1 | 4/2015 | Koseoglu et al. |
| 2016/0162664 | A1 | 6/2016 | Watanasiri et al. |
| 2018/0307803 | A1 | 10/2018 | Watanasiri et al. |

FOREIGN PATENT DOCUMENTS

| EP | 2 584 381 A1 | 4/2013 |
| EP | 2788754 | 10/2014 |
| EP | 3289495 | 11/2016 |
| JP | 10-185875 | 7/1998 |
| JP | H 11-508363 A | 7/1999 |
| JP | 2005-512051 A | 4/2005 |
| JP | 2008-513562 A | 5/2008 |
| JP | 6240091 | 11/2017 |
| JP | 201557747 | 11/2017 |
| WO | WO 1997/01096 A | 1/1997 |
| WO | WO 2006/030218 A1 | 3/2006 |
| WO | WO 2003/048759 A1 | 6/2013 |
| WO | WO 2013/106755 | 7/2013 |
| WO | WO 2016/178763 | 11/2016 |
| WO | 2018/200521 A2 | 11/2018 |

OTHER PUBLICATIONS

Poling, Bruce, E., et al., "Viscosity", *The Properties of Gases and Liquids* McGraw-Hill, 5th Ed., Chapter 9, pp. 9.77-9.90 (2001).
Riazi, M.R., "Characterization and Properties of Petroleum Fractions", *Petroleum Fractions*, ASTM International, Chapter 3, pp. 111-119 (2005).
Watt, Murray, R., et al., "Crude Assay", *Practical Advances in Petroleum Processing*, vol. 1, Chapter 3, Chang S. Hsu & Paul R. Robinson, Eds., Springer, pp. 103-116, (2006).
International Preliminary Report on Patentability for Int'l Application No. PCT/US2016/025929 entitled, "Method to Represent Metal Content in Crude Oils, Reactor Feedstocks, and Reactor Products" dated Nov. 7, 2017.
Riazi, M. R.; "Characterization and Properties of Petroleum Fractions;" Chapter 1—Introduction, pp. 1-29; American Society for Testing and Materials (2005).

(Continued)

*Primary Examiner* — G Steven Vanni
(74) *Attorney, Agent, or Firm* — Hamilton, Brook, Smith & Reynolds, P.C.

(57) ABSTRACT

A computer-implemented method of characterizing metal content and chemical composition of crude oil, including determining at least one respective organometallic class and subclass derived from physical and chemical property data for each organometallic class and crude oil physical and chemical property data and at least one segment type and segment number range of the segment type bound to each organometallic subclass. The method determines a relative ratio of each organometallic class and subclass that forms a chemical composition representative of the given crude oil, such that the determined relative ratio and the determined respective organometallic class and subclass, segment type, and segment number range form a characterization of the metal content and the chemical composition of the given crude oil, resulting in a display, as output to an end-user, of the formed characterization of the metal content and the chemical composition of the given crude oil.

20 Claims, 10 Drawing Sheets

(56) References Cited

OTHER PUBLICATIONS

International Preliminary Report of Patentability for Int'l Application No. PCT/US2013/021294 entitled: Method of Characterizing Chemical Composition of Crude Oil for Petroleum Refining Processing; dated Jul. 24, 2014.
Albahri, T. A., "Molecularly Explicit Characterization Model (MECM) for Light Petroleum Fractions," *Ind. Eng. Chem. Res.*, 44:9286-9298 (2005).
An, A. and Hao, X., "Generalized Predictive Control for a Precise Crude Oil Blending Process," *Proceedings of the IEEE, International Conference on Automation and Logistics* (2008).
Eckert, E. and Vaněk, T., "New Approach to the Characterization of Petroleum Mixtures Used in the Modelling of Separation Processes," *Computers & Chem. Eng.*, 30:343-356 (2005).
Gross, J. and Sadowski, G., "Perturbed-Chain SAFT: An Equation of State Based on a Perturbation Theory for Chain Molecules," *Ind. Eng. Chem. Res.* 40: 1244-1260 (2001).
Gross, J. et al., "Modeling Copolymer Systems Using the Perturbed-Chain SAFT Equation of State," *Ind. Eng. Chem. Res.* 42: 1266-1274 (2003).
Hudebine, D., et al., "Statistical Reconstruction of Gas Oil Cuts," *Oil & Gas Science Technology*, 66(3): 461-477 (2009).
International Preliminary Report on Patentability for International Application No. PCT/US2013/021294 entitled: "Method of Characterizing Chemical Composition of Crude Oil for Petroleum Refining Processing," dated Jul. 15, 2014.
Jaffe, S. B., et al., "Extension of Structure-Oriented Lumping to Vacuum Residua," *Ind. Eng. Chem. Res.*, 44:9840-9852 (2005).
Klein, et al., "Molecular Modeling in Heavy Hydrocarbon Conversions," *Taylor & Francis*, (2006).
McKenna, A., et al. "Unprecedented Ultrahigh Resolution FT-ICR Mass Spectrometry and Parts-Per-Billion Mass Accuracy Enable Direct Characterization of Nickel and Vanadyl Porphyrins in Petroleum from Natural Seeps," *Energy Fuels*, 28: 2454-2464 (2014).
NIST ThermoData Engine (NIST Standard Reference Database 103b, http://trc.nist.gov/tde.html) (several pages from website, printed Feb. 17, 2016).
Notification of Transmittal of the International Search Report and the Written Opinion of the International Searching Authority, or the Declaration, including International Search Report, issued in International Application No. PCT/US2013/021294, entitled: Method of Characterizing Chemical Composition of Crude Oil for Petroleum Refining Processing, dated Mar. 28, 2013.

Oil & Gas Journal Databook, 2006 Edition, PennWell Corporation, Tulsa, Oklahoma, 2006 (cover pages).
Peng, B, *Dissertation*, "Molecular Modelling of Petroleum Processes," University of Manchester Institute of Science and Technology (1999).
Pyl, S. P., et al., "Modeling the Composition of Crude Oil Fractions Using Constrained Homologous Series," *Ind. Eng. Chem. Res.* 50: 10850-10858 (2011).
Quann, R. J. and Jaffe, S. B., "Structured-Oriented Lumping: Describing the Chemistry of Complex Hydrocarbon Mixtures," *Ind. Eng. Chem. Res.*, 31: 2483-2497 (1992).
Saine Aye, M. M. and Zhang, N., "A Novel Methodology in Transforming Bulk Properties of Refining Streams into Molecular Information," *Chem. Eng. Sci.*, 60: 6702-6717 (2005).
Verstraete, J.J., et al., "Molecular Reconstruction of Heavy Petroleum Residue Fractions," *Chemical Engineering Science*, 65(1): 304-312 (2010).
Wu, Y. and Zhang, N., "Molecular Characterization of Gasoline and Diesel Streams," *Ind. Eng. Chem. Res.*, 49: 12773-12782 (2010).
Notification of Transmittal of the International Search Report and the Written Opinion of the International Searching Authority, or the Declaration, PCT/US2016/025929, "Method to Represent Metal Content in Crude Oils, Reactor Feedstocks, and Reactor Products", dated Jul. 6, 2016.
Sebor, G., et al., "Effect of the Type of Organometallic Iron and Copper Compounds on the Determination of Both Metals in Petroleum Samples by Flame Atomic-absorption Spectroscopy", *Analyst*, 107:1350-1355 (Nov. 1982).
Fernandez-Lima, et al., "Petroleum Crude Oil Characterization by IMS-MS and FTICR MS," Anal. Chem, vol. 81, No. 24, pp. 9941-9947, Dec. 15, 2009.
Hsu, et al., "Petroleomics: advanced molecular probe for petroleum heavy ends," Journal of Mass Spectrometry, vol. 46, No. 4, pp. 337-343, Mar. 24, 2011.
Qian et al., "Resolution and Identification of Elemental Compositions for More than 3000 Crude Acids in Heavy Petroleum by Negative-Ion Microelectrospray High-Field Fourier Transform Ion Cyclotron Resonance Mass Spectrometry," Energy and Fuels, vol. 15, No. 5, pp. 1505-1511, 2001.
Tanaka, et al., "Analysis of the Molecular Weight Distribution of Petroleum Asphaltenes Using Laser Desorption-Mass Spectrometry," Energy & Fuels, vol. 18, No. 5, pp. 1405-1413, 2004.
International Search Report and the Written Opinion of the International Searching Authority, International Application No. PCT/US2018/029135; entitled "Molecular Characterization Method and System", filed Apr. 24, 2018, dated Nov. 20, 2018.

* cited by examiner

| Molecular Class | Wt(%) | Carbon Number | CentroidTb (F) | p(API) | Segment Name | Segment Structure | Function | β | α |
|---|---|---|---|---|---|---|---|---|---|
| Porphyrin molecules | | | | | | | | | |
| Nickel porphyrins | 0.142 | 37 | 585.37 | 971.46 | Aromatic side ring | ◯ | Gamma | 1.15 | 0.1 |
| | | | | | Naphthenic side ring | ◯ | Gamma | 0.15 | 12.3 |
| | | | | | Side chain carbon number | $-C_nH_{2n+1}$ | Gamma | 0.391872 | 37.7768 |
| Vanadium porphyrins | 0.043 | 34 | 575.13 | 990.77 | Aromatic side ring | ◯ | Gamma | 1.15 | 0.1 |
| | | | | | Naphthenic side ring | ◯ | Gamma | 0.15 | 12.3 |
| | | | | | Side chain carbon number | $-C_nH_{2n+1}$ | Gamma | 0.115478 | 100 |

METHOD TO REPRESENT METAL CONTENT IN CRUDE OILS, REACTOR FEEDSTOCKS, AND REACTOR PRODUCTS

RELATED APPLICATION

This application (a) claims the benefit of U.S. Patent Application No. 62/155,791 filed May 1, 2015; and (b) is a continuation-in-part of U.S. application Ser. No. 13/740,095, filed Jan. 11, 2013, which claims the benefit of U.S. Provisional Application No. 61/644,792, filed on May 9, 2012 and U.S. Provisional Application No. 61/586,268, filed on Jan. 13, 2012. The entire teachings of the above applications are incorporated herein by reference.

BACKGROUND OF THE INVENTION

Each type of crude oil has unique molecular characteristics. These characteristics include different physical and chemical properties that can potentially affect the refining process. Typically, crude oils contain trace amounts of metal, such as vanadium or nickel. These metals become concentrated in the residual fractions of the refining process and can contaminate the products, poison catalysts, or corrode equipment. Refineries, therefore, seek to remove these metals prior to, or during, the refining process. Before a metal can be removed from crude oil, however, the refineries must identify the characteristics of the crude oil, including which metals are present and their concentrations. To do so, refineries can generate characterization data (or assay data) of a crude oil feedstock in a petroleum testing laboratory. Using the characterization (assay) data, refineries can estimate the characterization of a crude oil feedstock with respect to hydrocarbon content via a number of methods including use of a probability distribution function for hydrocarbon constituent molecules, as described in U.S. patent application Ser. No. 13/740,095 (submitted by Applicant), which is herein incorporated by reference in its entirety.

As global oil supply shifts towards heavy crude oils, refinery feeds will contain an increased amount of trace metals. Creation of efficient demetallation strategies will need an appropriate characterization to identify trace metals. A need for such characterization, therefore, exists.

SUMMARY OF THE INVENTION

Applicant's claimed invention solves the need for characterization of metal content in a crude oil. In particular, embodiments provide a detailed, molecular-level structural characterization that enables efficient demetellation processes to identify trace metals.

Accordingly, in an example embodiment, the present invention is a computer-implemented method of characterizing a chemical composition of crude oil, said method comprising: given a crude oil having a certain crude oil characterization data, in a processor: characterizing a metal content of the given crude oil by: (a) determining at least one respective organometallic class and subclass derived from physical and chemical property data for each organometallic class and crude oil physical and chemical property data; (b) determining at least one segment type and segment number range of the segment type bound to each organometallic subclass derived from physical and chemical property data for each segment type and crude oil physical and chemical property data; and (c) determining a relative ratio as a function of the certain crude oil characterization data, said relative ratio being of each organometallic class and subclass that forms a chemical composition representative of the given crude oil to each other organometallic class that form a chemical composition representative of the given crude oil, such that the determined relative ratio and the determined respective organometallic class and subclass, determined segment type, and respective segment number range of the segment type form a characterization of the metal content and the chemical composition of the given crude oil; and (d) displaying, as output to an end-user, the formed characterization of the metal content and the chemical composition of the given crude oil. The processor may also output the formed characterization as input to a demetellation process or other crude oil refining process, simulation, or system.

In addition, in some embodiments, the segment type includes a methyl segment, a zero-branch methylene segment, a one-branch methylene segment, a two-branch methylene segment, a carbocyclic segment, a heterocyclic segment, an aryl segment, a heteroaryl segment, a sulfide segment, or any combination thereof;

In addition, in some embodiments, the organometallic class is a porphyrin compound comprising a metal, such as vanadium or nickel;

In addition, in some embodiments, the method involves, for each organometallic class bound to the at least one segment type and for the respective segment number range, estimating physical and chemical property values as a function of organometallic class, segment type, and segment number range.

In addition, in some embodiments, determining the organometallic class, segment type, and the segment number range includes, for each organometallic class and segment type, identifying a probability distribution function for the organometallic class, segment type, and segment number range, including identifying scale and shape parameters of the probability distribution function. Optionally, the method further includes estimating the metal content and the chemical composition of the given crude oil as a function of the identified probability distribution functions and the relative ratio of each organometallic class, and estimating the physical and chemical properties of the given crude oil as a function of the estimated metal content and chemical composition. Further optionally: (a) the estimated physical properties of the given crude oil include any one of boiling point, density, viscosity, or any combination thereof (b) the estimated chemical properties of the given crude oil include any one of carbon content, hydrogen content, oxygen content, nitrogen content, sulfur content, vanadium content, nickel content, or any combination thereof or (c) determining the relative ratio of each organometallic class includes matching the estimated physical and chemical properties of the given crude oil against certain crude oil characterization data in order to determine the relative ratio of each organometallic class in the given crude oil to each other organometallic class that form a chemical composition representative of the given crude oil.

In addition, in some embodiments, the physical property data of the organometallic class includes any one of boiling point, density, and viscosity, or any combination thereof.

In addition, in some embodiments, the chemical property data of the organometallic class includes any one of carbon content, hydrogen content, oxygen content, nitrogen content, sulfur content, vanadium content, nickel content, or any combination thereof.

In addition, in some embodiments, the certain crude oil characterization data includes any one of boiling point, density, viscosity, or any combination thereof. Optionally, the certain crude oil characterization data further includes any one of paraffinic content, naphthenic content, aromatic content, carbon content, hydrogen content, nitrogen content, oxygen content, sulfur content, vanadium content, nickel content, C/H ratio, or any combination thereof.

In addition, in some embodiments, the method further comprises, in a computer, predicting physical and chemical properties of the given crude oil by representing the given crude oil using the characterized metal content and chemical composition of the given crude oil. Optionally, the method further comprises, in a computer, using at least one of the characterized chemical composition and the predicted physical and chemical properties of the given crude oil to plan, schedule, simulate, design, optimize, and/or control petroleum refining operations.

In addition, in some embodiments, the segment number range is between 0 and 3 inclusive for aromatic side rings, between 0 and 3 inclusive for naphthenic side rings, and between 1 and 60 inclusive for side chain carbons. For a given organometallic subclass, the segments (and respective segment number range) are molecular-level structural units (portions) of the class/subclass molecule and are distinct from whole molecule homologous series.

In addition, in some embodiments, the organometallic class is determined by the metal content.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIGS. 8A-B are screen views of display content in an example embodiment illustrating a formed characterization of a chemical composition according to principles of the present invention.

DETAILED DESCRIPTION OF THE INVENTION

Figure 1A:
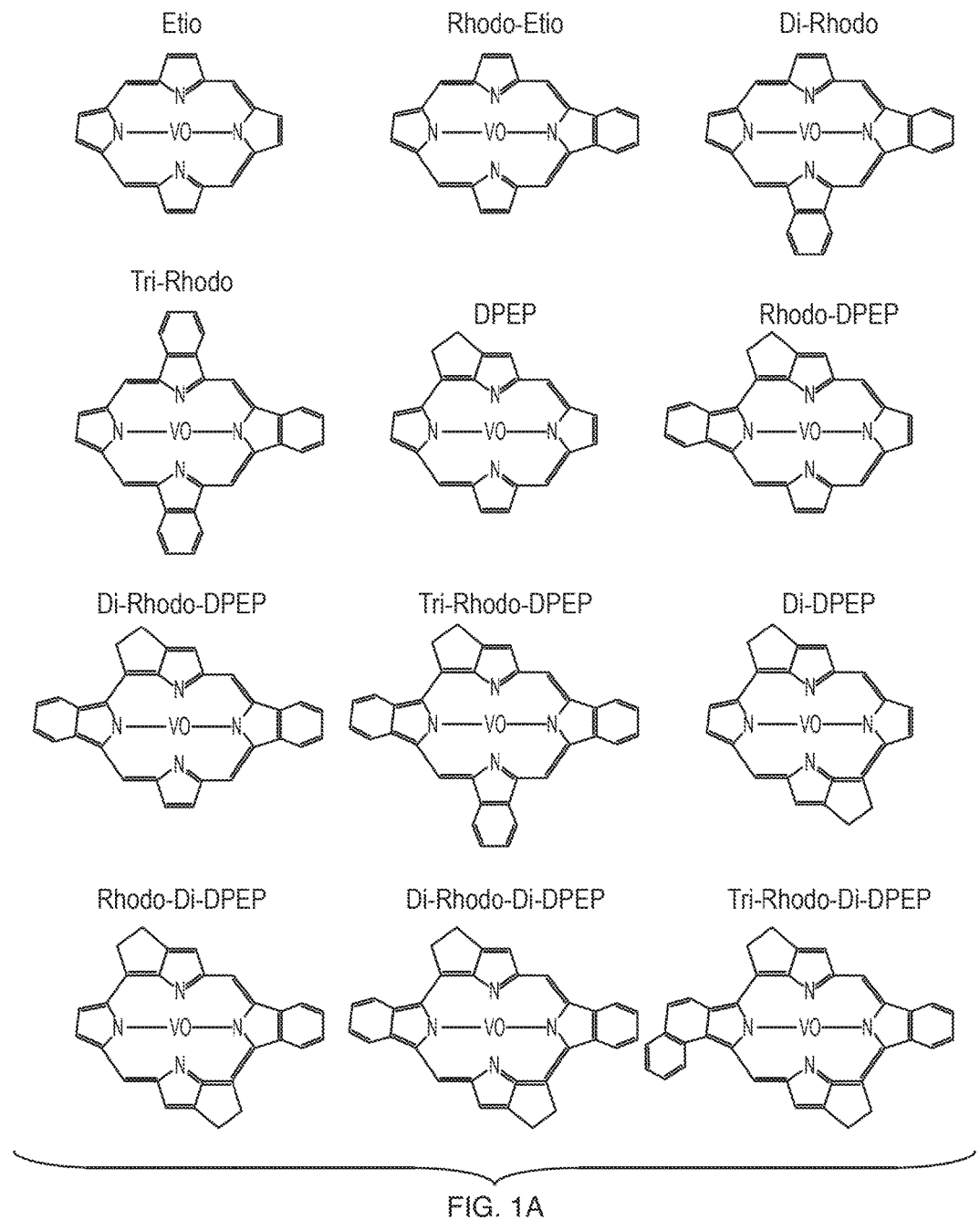
FIG. 1A illustrates an example organometallic class and subclasses thereof, which can be used in embodiments of the present invention.

A description of example embodiments of the invention follows.

Glossary

The term "alkyl," as used herein, refers to a saturated aliphatic branched or straight-chain monovalent hydrocarbon radical having the specified number of carbon atoms. Thus, "$C_1$-$C_6$ alkyl" means a radical having from 1-6 carbon atoms in a linear or branched arrangement. Examples of "$C_1$-$C_6$ alkyl" include, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl. Alkyl can be optionally substituted with $C_1$-$C_4$ alkyl, $C_1$-$C_6$ alkoxy, sulfide, and —N($R^1$)($R^2$) wherein $R^1$ and $R^2$ are each independently selected from —H and $C_1$-$C_3$ alkyl.

The term "methyl" and "methylene," as used herein, can also be used to refers to a mono-carbon "alkyl" as described herein. Examples of methyl or methylene include, —$CH_3$, —$CH_2$—,

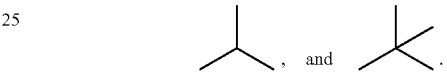

The term "cycloalkyl", as used herein, means saturated cyclic hydrocarbons, i.e. compounds where all ring atoms are carbons. Examples of cycloalkyl include, but are not limited to, cyclopropyl, cyclobutyl, cyclopentyl, cyclohexyl, and cycloheptyl. In some embodiments, cycloalkyl can optionally be substituted with one or more of hydroxyl, $C_1$-$C_{12}$ alkyl, or $C_1$-$C_{12}$ alkoxy.

The term "alkoxy", as used herein, refers to an "alkyl-O—" group, wherein alkyl is defined above. Examples of alkoxy group include methoxy or ethoxy groups.

The term "amino," as used herein, means an "—$NH_2$," an "$NHR_p$," or an "$NR_pR_q$," group, wherein $R_p$ and $R_q$ may be any of the alkyl, alkenyl, alkynyl, alkoxy, cycloalkyl, cycloalkoxy, aryl, heteroaryl, and bicyclic carbocyclic groups. In the present invention, the amino may be primary ($NH_2$), secondary ($NHR_p$) or tertiary ($NR_pR_q$). A (di)alkylamino group is an instance of an amino group substituted with one or two alkyls.

The term "aryl," as used herein, refers to an aromatic monocyclic or polycyclic (e.g. bicyclic or tricyclic) carbocyclic ring system. Thus, "$C_6$-$C_{18}$ aryl" is a 6-18 membered monocyclic or polycyclic system. Aryl systems include optionally substituted groups such as phenyl, biphenyl, naphthyl, phenanthryl, anthracenyl, or pyrenyl. An aryl can be optionally substituted. Examples of suitable substituents on an aryl include hydroxyl, $C_1$-$C_{12}$ alkyl, $C_6$-$C_{18}$ aryl, and (5-12 atom) heteroaryl.

In some embodiments, a $C_6$-$C_{18}$ aryl is selected from the group consisting of phenyl, indenyl, naphthyl, azulenyl, heptalenyl, biphenyl, indacenyl, acenaphthylenyl, fluorenyl, phenalenyl, phenanthrenyl, anthracenyl, cyclopentacyclooctenyl or benzocyclooctenyl. In some embodiments, a $C_6$-$C_{18}$ aryl is selected from the group consisting of phenyl, naphthalene, anthracene, 1H-phenalene, tetracene, and pentacene.

The term "carbocyclyl," as used herein, refers to a cyclic group with only ring carbon atoms. "Carbocyclyl" includes 3-12-membered saturated or unsaturated aliphatic cyclic hydrocarbon rings or 6-12-membered aryl rings. Carbocyclyls include cycloalkyl and aryl. Carbocyclyl can be a monocyclic or polycyclic ring system, with cycloalkyl rings fused to aryl rings. Carbocyclyl can optionally substituted in the same manner as alkyl or aryl, described herein.

The term "heteroaryl," as used herein, refers to aromatic groups wherein one or more carbon atoms is substituted with a heteroatom (O, S, or N). A (5-12 atom) heteroaryl group refers to a monocyclic or polycyclic ring system with 5 to 12 atoms, wherein at least one atom is a heteroatom. A heteroaryl group can be monocyclic or polycyclic, e.g. a monocyclic heteroaryl ring fused to one or more carbocyclic aromatic groups or other monocyclic heteroaryl groups. Examples of heteroaryl groups include, but are not limited to, pyridinyl, pyridazinyl, imidazolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, purinyl, oxadiazolyl, thiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, and azaindolyl. Suitable substituents for heteroaryl are as defined above with respect to aryl group.

The term "hetero," as used herein, refers to the replacement of at least one carbon atom member in a ring system with at least one heteroatom selected from N, S, and O. "Hetero" also refers to the replacement of at least one carbon atom member in a cyclic or acyclic system. A hetero ring system or a hetero acyclic system may have 1, 2, or 3 carbon atom members replaced by a heteroatom.

The term "organometallic," as used herein, refers to an organic chemical compound containing at least one bond between a nitrogen atom and a metal.

The term "sulfide," as used herein, refers to $C_1$-$C_{30}$ alkyl-S— or —S—$C_1$-$C_{30}$ alkyl.

Molecular Based Characterization of Metal Content

A molecular structure-based approach to characterizing crude oil and petroleum fractions with respect to hydrocarbon content is presented in U.S. patent application Ser. No. 13/740,095, which is herein incorporated by reference in its entirety. The method uses individual hydrocarbon molecules as a vector of incremental structural features that can describe the composition, reactions, and properties of petroleum mixtures. Chemical compositions of the individual hydrocarbon molecules are inferred from analytical results (assay data) of the crude oil. These analytical results provide physical properties such as the boiling point, the density, and the vapor pressure, as well as chemical properties, such as atom content of the crude oil. This methodology allows refineries to estimate the chemical composition of the crude oil, as well as estimate the physical properties such as the boiling point, density, and vapor pressure for both the crude oil and various fractions found at different stages of the refining process.

There remains a need, however, for methods that allow refineries to characterize a metal composition including metal content. A molecular structure-based approach to characterizing crude oil and petroleum fractions that contain metal content is presented herein. Analytical results of crude oil can provide physical properties such as the boiling point, the density, and the vapor pressure, and can also provide chemical properties, such as metal content of the crude oil. The presence of a metal can be identified, for example, by Fourier transform ion cyclotron mass spectrometry (FT-ICR MS) of the crude oil. This data can further be used to determine the organometallic complexes in which the metals are associated.

Metal complexes in crude oils are generally present in porphyrin structures. Examples of porphyrin structures are cholophyll or Heme B. Generally, the porphyrin structure is a planar, cyclic molecule that contains four pyrrolic nitrogens linked with methine bridges (=CH—), wherein the metal atom, located in the center of the molecule is bound to nitrogen atoms. An example porphyrin structure, porphine, is seen in structural formula (I):

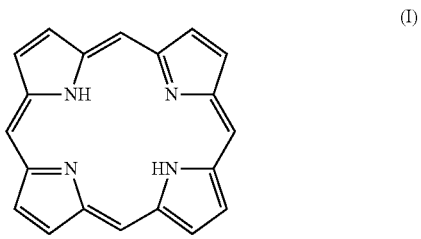 [SMILES: C1=Cc2cc3ccc(cc4nc(cc5ccc(cc1n2)[nH]5)C=C4)[nH]3]

(I)

Substitution of the eight β-hydrogens results in different structures that exist as a homologous series in petroleum. The porphyrin of structural formula (I), therefore, is the simplest porphyrin present in crude oil.

A metal can form a complex with the porphyrin, creating an organometallic species. Many different metals can be coordinated with the porphyrin, including magnesium, iron, nickel, and vanadium. In crude oils, porphyrin structures such as the structure seen in structural formula (I) are often seen coordinated with vanadium and nickel. Accordingly, nickel and vanadium are the most abundant metal types, creating porphryins as seen in example structural formulas (II) and (III):

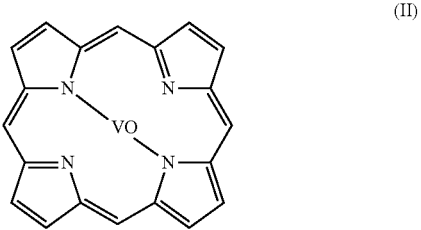

(II)

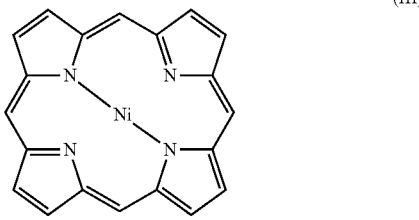

(III)

Figure 1B:
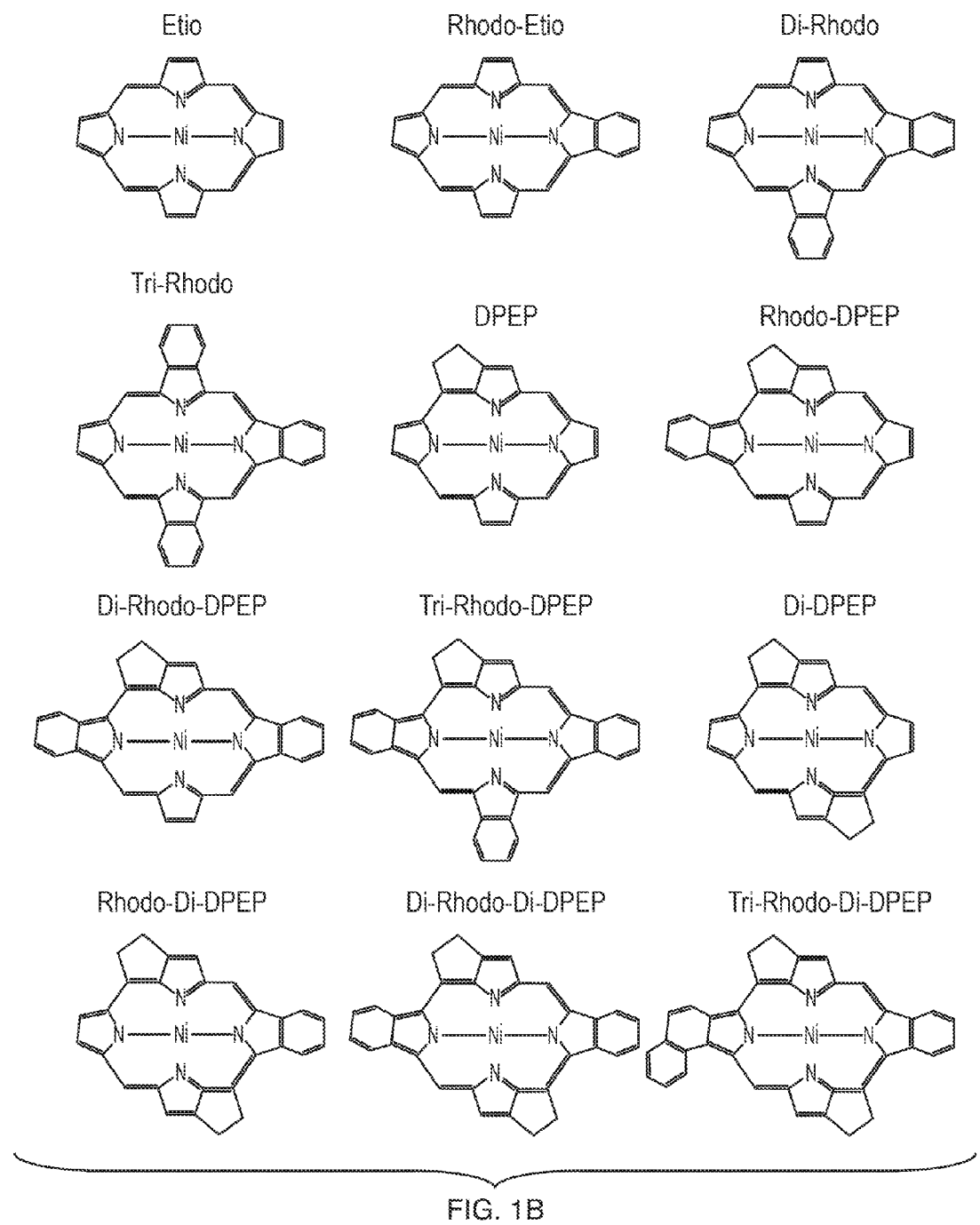
FIG. 1B illustrates another example organometallic classes and subclasses thereof, which can be used in embodiments of the present invention.

As used herein, reference to an organometallic "class" refers to an organometallic molecule containing a specific metal. The classes differ with respect to the metal that is bound to the organic compound. For example, the porphyrin of structural formula (II) is directed to one organometallic class, whereas the porphyrin of structural formula (III) is directed to a separate organometallic class. As used herein, an organometallic "subclass" is a core structure within an organometallic class, such as those described below with respect to FIGS. 1A-B. Names for subclasses are as indicated in FIGS. 1A and 1B, which provide prefixes to the term "porphyrin." For example, the indicated "Etio" subclass core structure refers to an "etioporphyrin" core as shown in FIGS. 1A and 1B. The nomenclature in FIGS. 1A and 1B is adopted by Applicant for convenience even though it may not be consistent (or entirely consistent) with that used in porphyrin literature (e.g., the "Etio" core structure, as that term is used herein, does not have methyl or ethyl substituents along the ring).

The porphyins in crude oil are not limited merely to the molecules drawn in structural formulas (II)-(III), and FIGS. 1A-B, however. As stated above, the substitution of any one of the eight β-hydrogen results in a different compound within an organometallic class or subclass. The substitution can be, for example, an alkyl or methylene chain optionally substituted with a monocyclic or fused polycyclic carbocyclyl, aryl, or heteroaryl, such as, for example, the compound of structural formulas (IV)-(VI):

probability distribution functions for each organometallic class and subclass, as well as for the substitutions ("segments," described further below), (a) is less burdensome than traditional methods in terms of the amount of experimental data needed for computations of physical properties of crude oil, and (b) enables easier adjustment of the profile (i.e., composition) of a given crude oil, e.g., to represent drift in properties due to a different depth from which the crude oil is produced. The easier adjustment of the profile is due to the approach in the present invention using the same profile and adjusting the probability distribution functions to match the change in physical and chemical properties accordingly. Use of model compounds created from organometallic classes, subclasses and respective segments, therefore, can be used with the crude oil characterization (assay) data to provide characterization of a given crude oil and to provide estimates of physical and chemical properties of said crude oil in a more robust fashion.

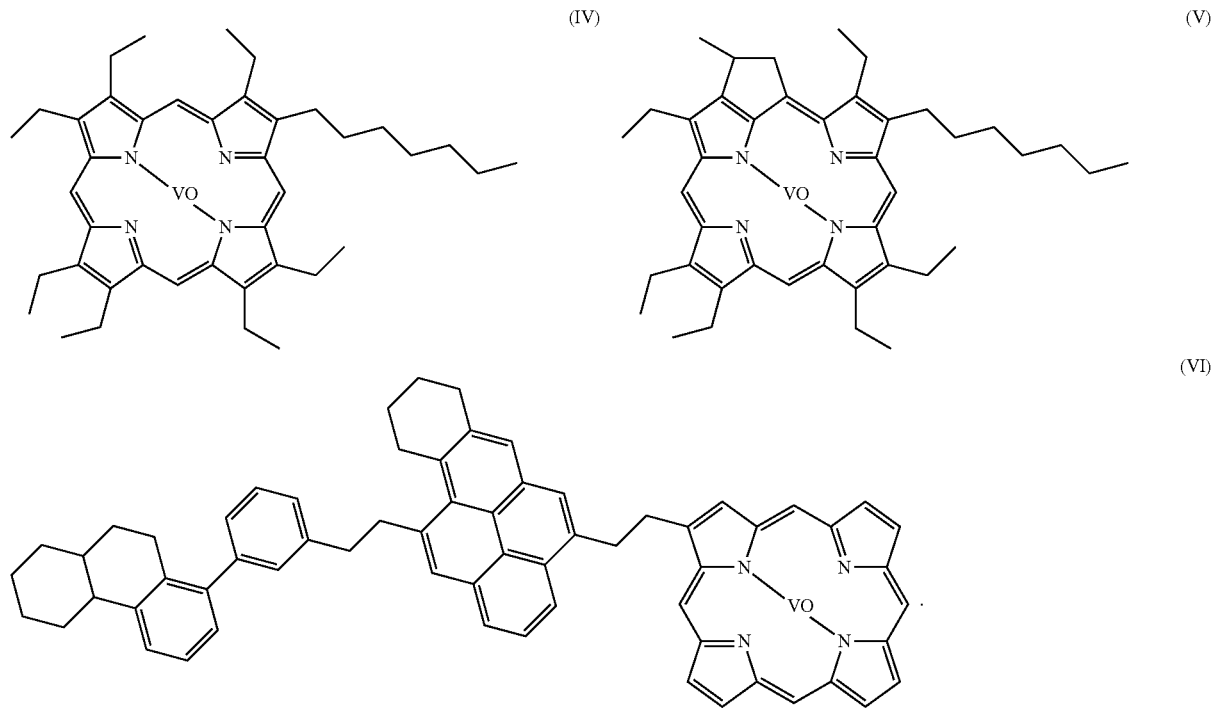

The example structural formula (IV) recites use of alkyl linking molecules, thus creating a methylene chain, e.g., —CH2 groups are linked to form an alkyl chain. It should be understood that heteroatoms such as sulfur, nitrogen, or oxygen can be present as well in both the chain and the cyclic moieties. These side chains and cyclic moieties are referred to as "segments" and are described in more detail below.

A crude oil, therefore, contains a mixture of these organometallic classes and subclasses with various substitutions at the eight β-hydrogen positions. To determine the compositions of these organometallic compounds, probability distribution functions are used. To determine the length of the side chain (e.g., a side chain of —CH2 units) and number of other segments (segment frequency) (e.g., of aromatic side rings or naphthenic side rings) bound to each subclass, probability distribution functions are also used. Use of As an example, for the purpose of identifying the probability of the occurrences (hence compositions) of each type of core, a single core structure (e.g., the first structure in FIGS. 1A and 1B—namely, the Etio form of the porphyrin complex) can be used as the base from which all other cores can be constructed by adding on segments. In some embodiments, three types of segments can be used: aromatic side ring, naphthenic side ring, and side chain carbon number. The probability of aromatic side ring, can be used to provide a relative composition of rhodo-related subclasses. The probability of naphthenic side rings can give a relative composition of DPEP-related subclasses. These two ring-segments, can allow for creating other cores from the base core. Finally, the side chain carbon number can indicate a chain length—thus allowing molecules (compounds) to be created from cores. Multiplying these probabilities and the class weight can give a composition of each compound.

Methods used to compute the composition of each compound from the distribution function and class weight are described in U.S. Patent Publication No. 2013185044, published Jul. 18, 2013, entitled "Method of Characterizing Chemical Composition of Crude Oil for Petroleum Processing," U.S. patent application Ser. No. 13/740,095, which is hereby incorporated by reference in its entirety.

Where the added segment numbers are all zero, then the core structure of the base subclass is obtained. Thus, with respect to the previous paragraph, for example, if the probability of aromatic side rings, naphthenic sides rings, and side chain carbons are all zero, then the core structure of the Etio subclass is obtained, namely etioporphyrin (as shown in FIGS. 1A and 1B). When the probability of side chain carbons is nonzero, this corresponds to additional compounds within the Etio subclass.

Physical and chemical properties of various classes and subclasses of organometallic molecules for crude oil and petroleum fractions are not available to the public and are estimated. Limited data for Porphine were obtained from NIST ThermoData Engine (NIST Standard Reference Database 103b), NIST, 647.01, 325 Broadway Boulder, Colo. 80305-3337, 2015.

Physical properties can also be estimated with the segment-based PC-SAFT equation of state that enables rigor, accuracy, and thermodynamic consistency in the calculation of fundamental physical properties such as vapor pressure, boiling point, density, and heat capacity. See J. Gross, G. Sadowski, Perturbed-Chain SAFT: An Equation-of-State Based on a Perturbation Theory for Chain Molecules, Ind. Eng. Chem. Res. 2001, 40, 1244-1260 (hereinafter "Gross 2001"); J. Gross, G. Spuhl, F. Tumakaka, G. Sadowski, Modeling Copolymer Systems Using the Perturbed-Chain SAFT Equation of State, Ind. Eng. Chem. Res. 2003, 42, 1266-1274 (hereinafter "Gross 2003"). Exact makeup of a given crude oil in terms of various organometallic classes and subclasses can be adjusted so that calculated physical and chemical properties can best match available physical and chemical property measurements of the crude oil, such as metal content (e.g., vanadium content, nickel content, etc.), true boiling point, API gravity, viscosity, C/H ratio, etc. Missing properties of the crude oil assay are then estimated from the chemical compositions and the properties of the organometallic classes and subclasses. Utilities of this approach are further validated with the extensive crude oil assays available to the Applicant. Available references include, for example, Oil & Gas Journal Databook, 2006 Edition, PennWell Corporation, Tulsa, Okla., 2006.

Accordingly, selecting the appropriate organometallic classes and subclasses and practical rules for automatically generating and constructing model molecules from structural segments is key in a molecular structure-based approach to characterizing metal content of crude oil and petroleum fractions. FIG. 1A illustrates twelve example organometallic subclasses (core structures) of the same organometallic class which contain a vanadium atom. FIG. 1B illustrates twelve example organometallic subclasses (core structures) of the same organometallic class which contain a nickel atom. Use of these compounds in the present invention is beneficial as the literature values for the porphyrin compounds without the chelated metal are known.

The physical and chemical properties of these porphyrin structures can then be estimated by PC-SAFT using known or determined parameters for the porphine of structural formula (I) and the desired metal atom (e.g., vanadium or nickel). In an example embodiment, the basic porphyrins of structural formulas (II) and (III) are represented by the porphine of structural formula (I) combined with a metal, such as vanadium or nickel (to create structural formulas (II) and (III), respectively). The PC-SAFT parameters for the porphine of structural formula (I) is determined from experimental data of the known, physical properties of porphine, including, for example, the boiling point.

The PC-SAFT parameters of a porphine-metal complex (e.g., the compounds of structural formulas (II) and (III)) are determined using available crude assay data for which said metal is available. For example, using the lowest boiling point cut of available crude assay data for which metal content is available, the PC-SAFT parameters for the porphine-metal complex can be determined.

Once the organometallic classes and subclasses are determined, segment type and the segment number range are determined per class/subclass. The segments are bound to the organometallic subclasses (core structures) of the organometallic classes. Given that each of eight different β-hydrogens can be substituted on each organometallic class and subclass, the number of potential model compounds can grow exponentially. To minimize the number of model molecules required to fully characterize physical and chemical properties, the segment number range can be limited. In an example embodiment, the segment number range is between 1 and 60, inclusive. The proper per class/subclass segment type, segment number range, and their respective probability distribution functions can be determined and optimized with the aim to provide a comprehensive and practical representation of diverse physical and chemical properties of crude oil such as metal content (e.g., vanadium content, nickel content, etc.), boiling point, density, viscosity, aromatic content, carbon content, hydrogen content, C/H ratio, sulfur content, nitrogen content, etc.

The segment number range is the range within which the number of each segment types of a class/subclass can be varied. For example, in some embodiments, the 3 segment types related to metal content, and associated number ranges, can be as follows: Aromatic side ring: 0-3; Naphthenic side ring: 0-3; Side chain carbon: 1-60.

As stated above, the porphyrin structures of FIGS. 1A-B can be substituted with various segments. In an example embodiment, the segment type bound to the organometallic classes and subclasses can be a methyl segment, a zero-branch methylene segment, a one-branch methylene segment, a two-branch methylene segment, a carbocyclic segment, a heterocyclic segment, an aryl segment, a heteroaryl segment, a sulfide segment, or any combination thereof.

Examples of these molecular structural repeating units or "segments" that are selected to make up the model hydrocarbon constituent molecules are illustrated below. Here, the —CH$_3$ segment is the methyl end group, the —CH$_2$— segment is the zero-branch methylene repeat group, the

segment is the one-branch methylene group, the

segment is the two-branch methylene group. As defined above, a segment can also be a sulfide or a ring system (e.g., a carbocycle, a heterocycle, an aryl, or a heteroaryl). Examples of ring systems useful in the present invention include:

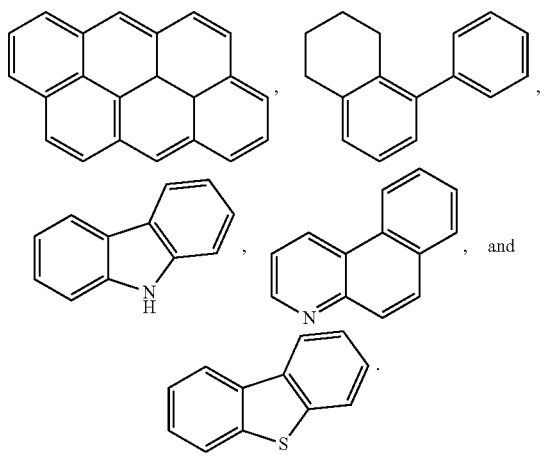

Figure 2:
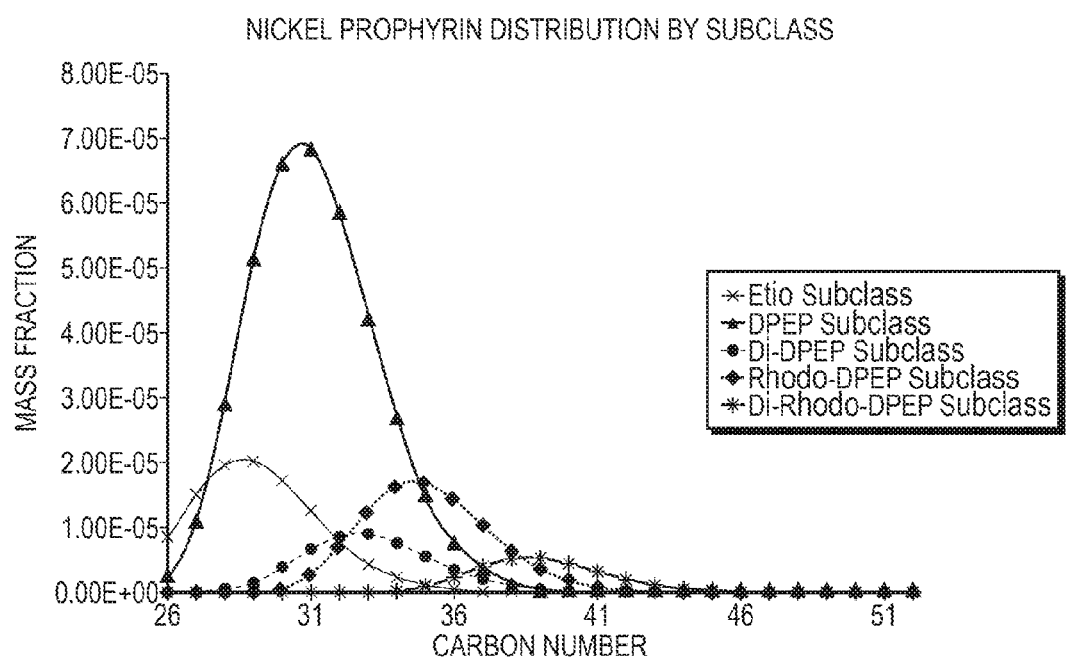
FIG. 2 is a plot of nickel abundance in a given crude oil. The plot illustrates the distribution of nickel porphyrin subclasses as compared to the number of carbon atoms in a sample crude oil. The subclasses are as indicated.

Characterization of a Crude Oil or Petroleum Fraction Using a Molecule Based Approach To identify the organometallic subclasses of the organometallic class, probability distribution functions and associated parameters for the structural segments are established through systematic investigation. With respect to the metal content, a metal abundance plot obtained from the FT-ICR-MS measurements of the crude or petroleum fractions shows relative abundance of different compounds of an organometallic class as a function of carbon numbers. An example plot for the distribution of nickel porphyrin subclasses can be seen in FIG. 2.

From this data, an algorithm determines the probabilities of segment types and segment number ranges. Example probability distribution functions can include, for example, a gamma distribution function which is a two parameter family of probability distributions of the form $$p(n) = \frac{(n-L)^{\alpha-1} \cdot e^{-\frac{n-L}{\beta}}}{\beta^{\alpha} \cdot \Gamma(\alpha)} \tag{1}$$

where p(n) is the probability of the sample value n; L is the location, the starting point of the probability distribution function; $\alpha$ is the shape factor; $\beta$ is the scale parameter; and $\Gamma(\alpha)$ is the gamma function. The relative contents of the molecules are then identified from regression against assay physical and chemical data such as true boiling point, API gravity, viscosity, metal content, and aromatic content of selected distilled fractions as described below.

The segment-based PC-SAFT equation-of-state (EOS) is used to develop a thermodynamically consistent framework to accurately calculate physical properties for the model hydrocarbon constituent molecules and their mixtures. See Gross 2001; Gross 2003. Segment-based parameters required to characterize the segments that build up the organometallic molecules used to represent metal content of crude oil are thereby obtained for PC-SAFT. These segment-based PC-SAFT parameters include segment ratio, segment size, and segment energy parameters. See Gross 2003. These parameters are identified from regression of experimental data on vapor pressure, liquid density and liquid heat capacity of hundreds of hydrocarbon compounds made up of these segments.

These segment parameters together with the PC-SAFT EOS provide a rigorous and predictive thermodynamic framework based on principles of statistical mechanics. This thermodynamic framework enables systematic exploration of different classes of molecules with various types of segments and segment number ranges. Of particular significance is the unique ability of the PC-SAFT EOS to accurately correlate and predict vapor pressure and liquid density simultaneously. In contrast, typical cubic equations of state such as Peng-Robinson and Redlich-Kwong-Soave are only capable of calculating vapor pressure accurately. These cubic equations of state are incapable of calculating liquid density accurately.

Using the characterization (assay) data, the present invention utilizes an nonlinear regression algorithm to determine the probabilities of segments, e.g., naphthanic side rings, aromatic side rings, methylene side chains, etc., which are then used to calculate compositions of the porphyrin compounds (e.g., the organometallic classes and subclasses together with the segment types and segment number ranges bound to said organometallic classes and subclasses). Use of FT-ICR-MS measurements provide guidance as to the relative abundance of the different compounds of organometallic classes. Therefore, by determining the relative ratio of each organometallic class that forms the chemical composition of the crude oil, a characterization of the crude oil can be obtained. For use of FT-ICR-MS, see Amy M. McKenna, et al. "Unprecedented Ultrahigh Resolution FT-ICR Mass Spectrometry and Parts-Per-Billion Mass Accuracy Enable Direct Characterization of Nickel and Vanadyl Porphyrins in Petroleum from Natural Seeps," *Energy Fuels*, 28: 2454-2464 (2014). The regression algorithm used in the invention seeks to minimize the sum of squares difference between the characterization (assay) data and the corresponding computed physical and chemical properties that are obtained from the calculated compositions of the compounds and their physical and chemical properties. Based on the sum of squares difference, adjustable parameters are adjusted until the error is smaller than a pre-prescribed tolerance (e.g., 1e-5).

Once characterization (assay) data is received, the system or a user can also "fix" certain variable parameters when creating the composition from the model compounds. Fixing requires certain parameters (e.g., the % by weight of nickel porphyrins, the shape and size of the probability distribution function, etc.) to remain constant, and forces the system to identify a mixture of compounds that conforms to those fixed parameters. This reduces the number of adjustable parameters since metal content data are generally quite limited for a given crude oil. Using a combination of fixed and adjusted parameters, the organometallic and other hydrocarbon compounds in a given crude oil can be determined.

Generating Complete Assays and Properties

Given the molecular distribution parameters for crude oil, various molecular thermodynamic models such as PC-SAFT EOS, group contribution methods, and other methods can be applied to predict a wide variety of physical and chemical properties for crude oil including vapor pressure, density, viscosity, metal content (e.g., vanadium content, nickel content, etc.), paraffin content, naphthene content, aromatic content, carbon content, hydrogen content, C/H ratio, asphaltene content, carbon residue, sulfur content, nitrogen content, total acid number, molecular weight, heat capacity, heating value, heat of vaporization, cloud point, aniline point, wax content, etc. Conversely, if data are available for these physical and chemical properties, they can be used in the regression methodology described above to identify optimal molecular distribution parameters.

Figure 3:
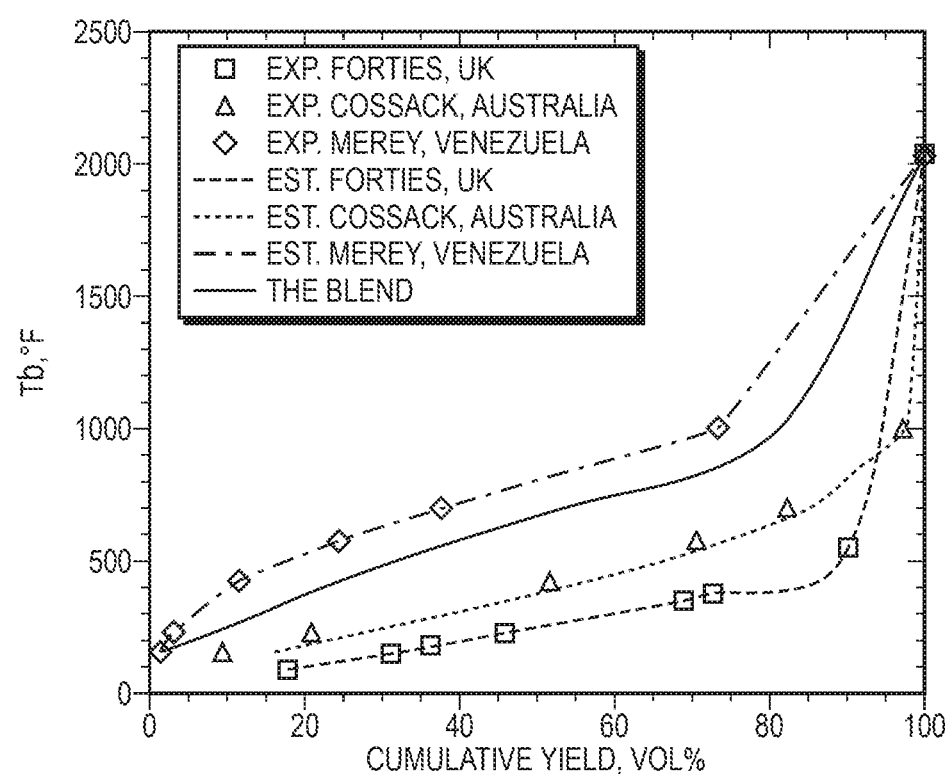
FIG. 3 is a model-predicted true boiling point for a blend made from three crude oils, according to embodiments of the present invention.
Figure 4:
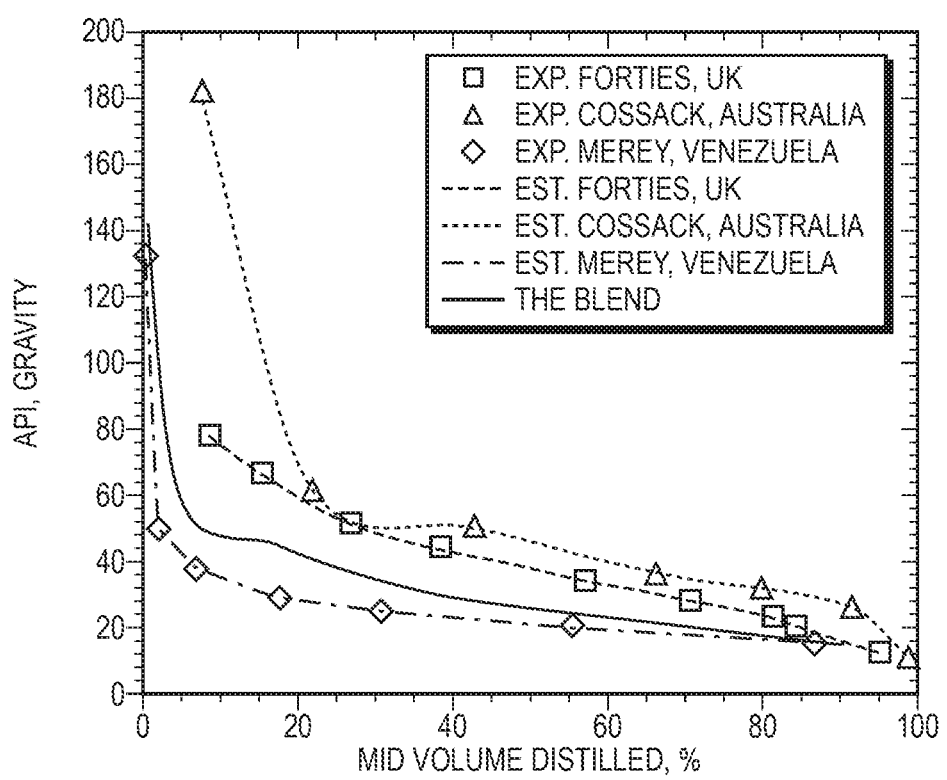
FIG. 4 is a model-predicted API gravity for a blend made from three crude oils, according to embodiments of the present invention.

The molecular distribution parameters for crude oil further provide the molecular basis for crude oil blending calculations. Traditionally, an arbitrary set of pseudocomponents is applied to all crude oil to be blended, and crude blending is then performed on the pseudocomponent level. In contrast, no such pseudocomponents are required for crude blending with the molecular structure-based approach of the present invention. Here, the chemical compositions of blended crude oil are the sum of the chemical compositions of individual crude oils. Assay properties of a blend can be rigorously computed based on its molecular representation without the need to go through the artificial step of generating pseudocomponents. FIGS. 3 and 4 show the present invention model-predicted true boiling point and API gravity, respectively, for a blend made from three crude oils. The same methodology described above for modeling crude oil assays and their blends can be applied directly to blending petroleum fractions which have limited boiling point ranges.

Molecular Based Methodology for Planning, Scheduling, and Process Simulation

As mentioned earlier, crude assays are often used to generate a certain limited number of "pseudocomponents" or "hypothetical components" and their compositions are then used to represent the petroleum mixtures for the purpose of planning, scheduling, and process simulation of petroleum refining processes such as fractionations and reactions. Properties of pseudocomponents are defined to mimic a fraction of the crude assay, i.e., with specific ranges of boiling point and specific gravity. The molecular (and in particular molecular structural) characterization approach offers not only a superior methodology to correlate and predict full assays that subsequently can be used to generate "pseudocomponents," it also offers an important new alternative to this traditional "pseudocomponent" approach for planning, scheduling and process simulation. Specifically, the model molecules and their compositions associated with the molecular distribution parameters can be used directly to represent crude oil and petroleum fractions in planning, scheduling, and process simulation of petroleum refining operations.

Computer Implementation

Figure 5:
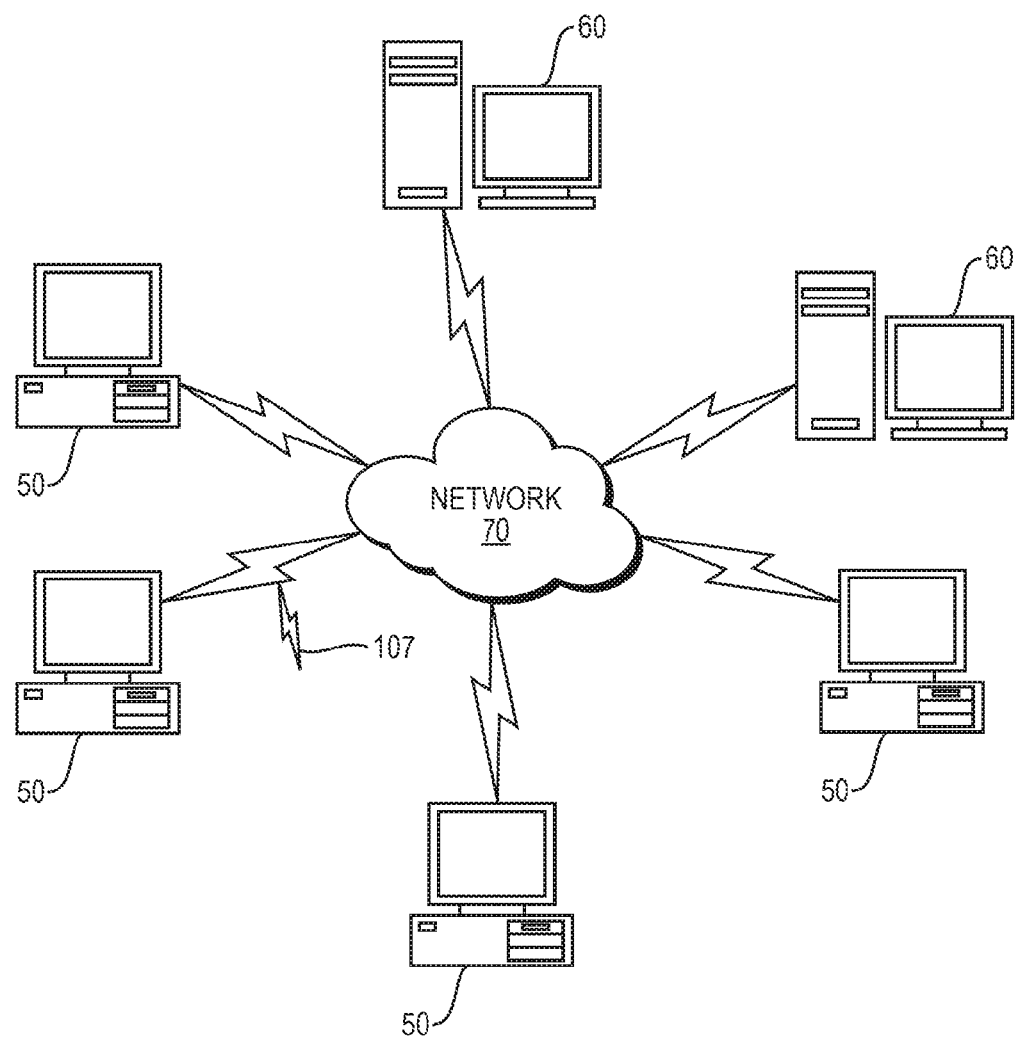
FIG. 5 is schematic view of an example computer network in which embodiments of the present environment may be implemented.

FIG. 5 illustrates a computer network or similar digital processing environment in which the present invention may be implemented.

Client computer(s)/devices 50 and server computer(s) 60 provide processing, storage, and input/output devices executing application programs and the like. Client computer(s)/devices 50 can also be linked through communications network 70 to other computing devices, including other client devices/processes 50 and server computer(s) 60. Communications network 70 can be part of a remote access network, a global network (e.g., the Internet), a worldwide collection of computers, Local area or Wide area networks, and gateways that currently use respective protocols (TCP/IP, Bluetooth, etc.) to communicate with one another. Other electronic device/computer network architectures are suitable.

Figure 6:
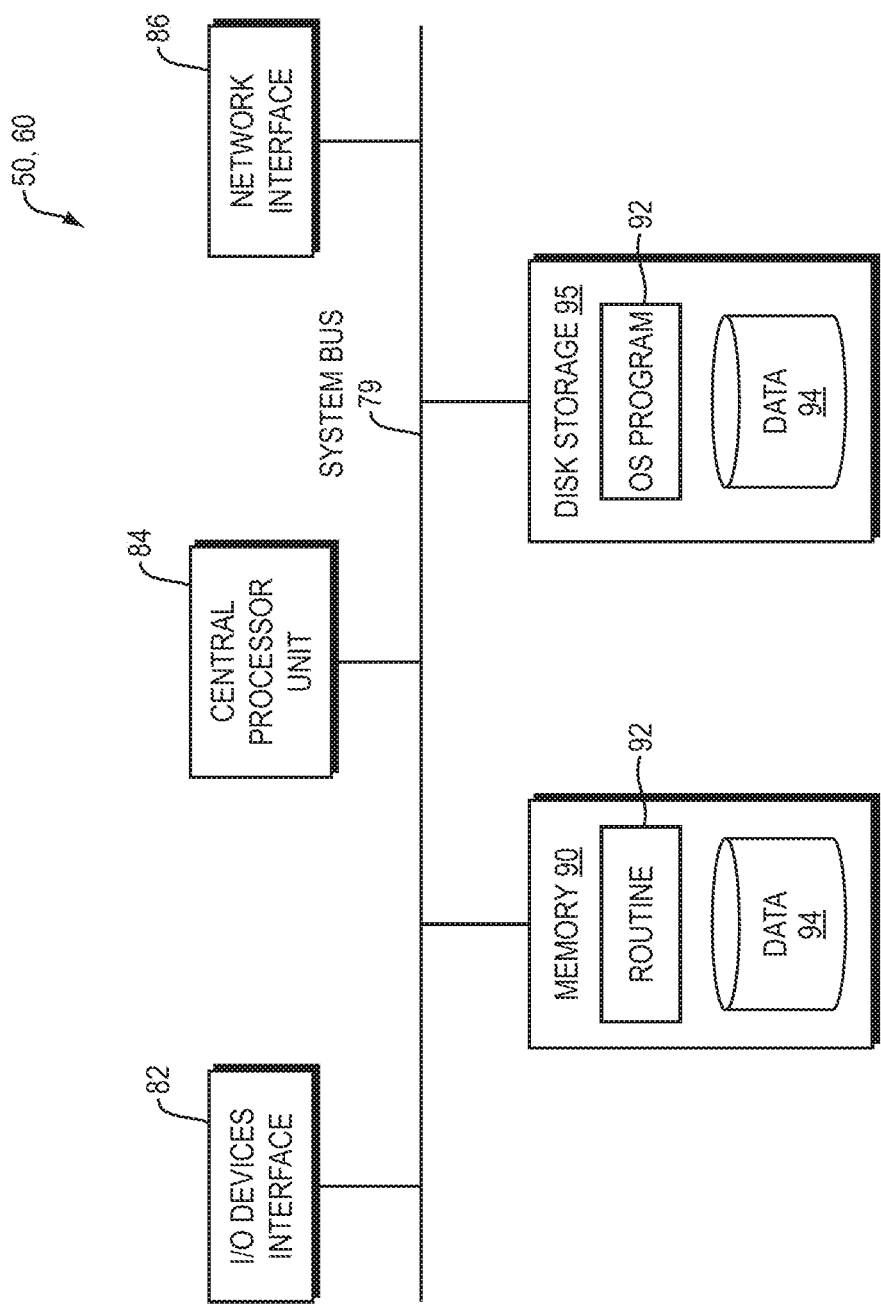
FIG. 6 is a block diagram of the internal structure of a computer in the computer network of FIG. 5.

FIG. 6 is a diagram of the internal structure of a computer (e.g., client processor/device 50 or server computers 60) in the computer system of FIG. 5. Each computer 50, 60 contains system bus 79, where a bus is a set of hardware lines used for data transfer among the components of a computer or processing system. Bus 79 is essentially a shared conduit that connects different elements of a computer system (e.g., processor, disk storage, memory, input/output ports, network ports, etc.) that enables the transfer of information between the elements. Attached to system bus 79 is I/O device interface 82 for connecting various input and output devices (e.g., keyboard, mouse, displays, printers, speakers, etc.) to the computer 50, 60. Network interface 86 allows the computer to connect to various other devices attached to a network (e.g., network 70 of FIG. 5). Memory 90 provides volatile storage for computer software instructions 92 and data 94 used to implement an embodiment of the present invention (e.g., virtual assay engine, crude oil assay modeler, and supporting code 700 detailed above and below). Disk storage 95 provides non-volatile storage for computer software instructions 92 and data 94 used to implement an embodiment of the present invention. Central processor unit 84 is also attached to system bus 79 and provides for the execution of computer instructions.

In one embodiment, the processor routines 92 and data 94 are a computer program product (generally referenced 92), including a computer readable medium (e.g., a removable storage medium such as one or more DVD-ROM's, CD-ROM's, diskettes, tapes, etc.) that provides at least a portion of the software instructions for the invention system. Computer program product 92 can be installed by any suitable software installation procedure, as is well known in the art. In another embodiment, at least a portion of the software instructions may also be downloaded over a cable, communication and/or wireless connection. In other embodiments, the invention programs are a computer program propagated signal product 107 embodied on a propagated signal on a propagation medium (e.g., a radio wave, an infrared wave, a laser wave, a sound wave, or an electrical wave propagated over a global network such as the Internet, or other network(s)). Such carrier medium or signals provide at least a portion of the software instructions for the present invention routines/program 92.

In alternate embodiments, the propagated signal is an analog carrier wave or digital signal carried on the propagated medium. For example, the propagated signal may be a digitized signal propagated over a global network (e.g., the Internet), a telecommunications network, or other network. In one embodiment, the propagated signal is a signal that is transmitted over the propagation medium over a period of time, such as the instructions for a software application sent in packets over a network over a period of milliseconds, seconds, minutes, or longer. In another embodiment, the computer readable medium of computer program product 92 is a propagation medium that the computer system 50 may receive and read, such as by receiving the propagation medium and identifying a propagated signal embodied in the propagation medium, as described above for computer program propagated signal product.

Generally speaking, the term "carrier medium" or transient carrier encompasses the foregoing transient signals, propagated signals, propagated medium, storage medium and the like.

Figure 7:
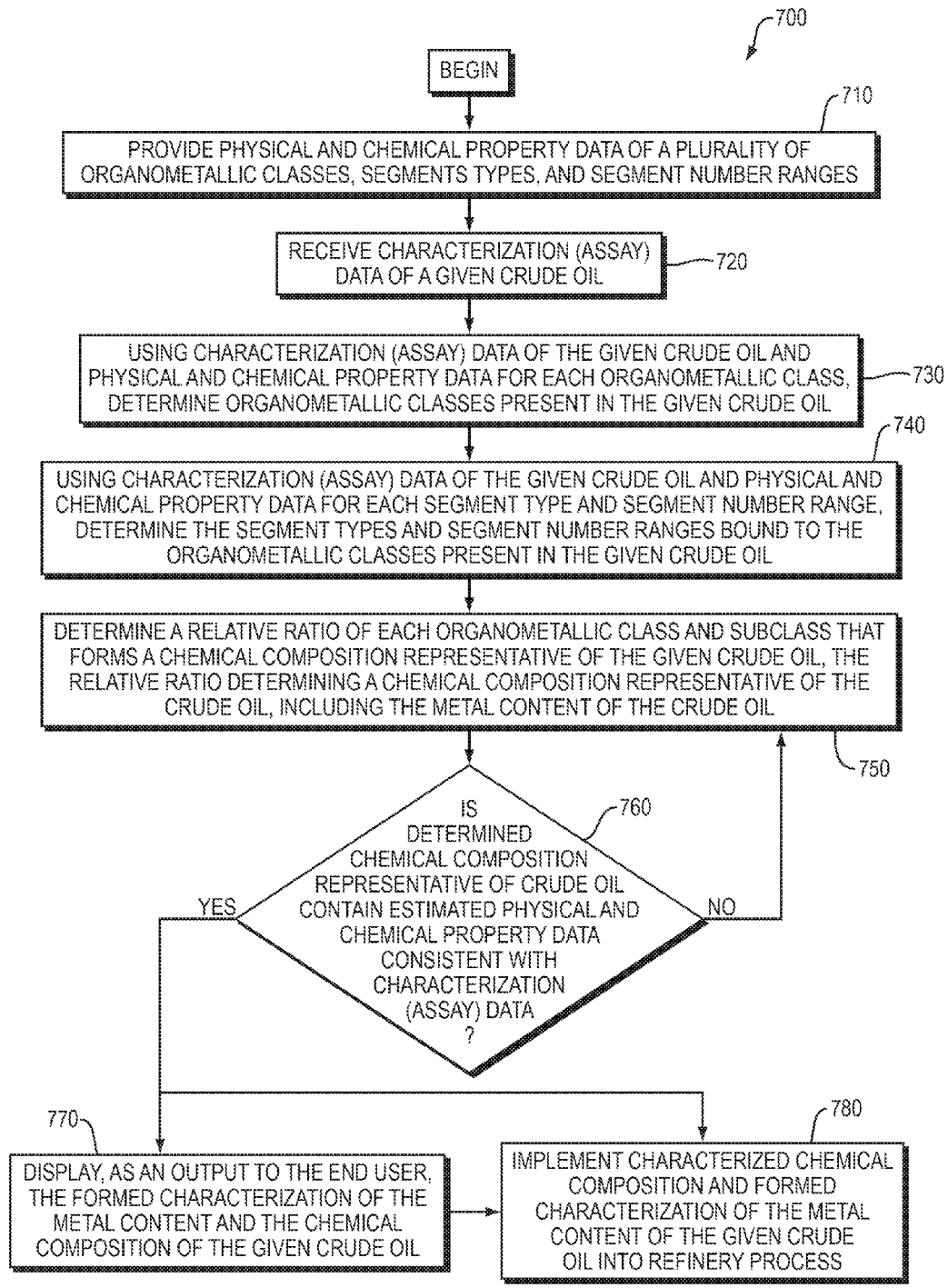
FIG. 7 is a flow diagram of an example embodiment of a computer implemented method of characterizing a metal content of a given crude oil, according to principles of the present invention.

FIG. 7 is a flow diagram (processor routine) 700 of an example embodiment of a computer-implemented method of characterizing a metal content of a given crude oil (sample) and updating refinery process in light of the characterized metal content of the crude oil. At 710, the user, computer system 50, 60, or processor 700 provides physical and chemical property data for a plurality of the organometallic class and subclasses and other hydrocarbon classes and subclasses, segment types, and segment number ranges described above. The physical property data of the organometallic classes and subclasses can include, for example, any one of boiling point, density, and viscosity, or any combination thereof. The chemical property data of the organometallic classes and subclasses can include, for example, any one of carbon content, hydrogen content, oxygen content, nitrogen content, sulfur content, vanadium content, nickel content, or any combination thereof.

At 720, computer system 50, 60 or processor receives characterization (assay) data of the given crude oil (sample). As described above this characterization (assay) data can be provided, for example, by ASTM procedures, GC, GC-MS, or FT-ICR-MS, and identify physical properties such as a boiling point, a density, a viscosity, a vapor pressure, or any combination thereof; and chemical properties including the percent weight of paraffinic content, naphthenic content, aromatic content, carbon content, hydrogen content, nitrogen content, oxygen content, sulfur content, metal content (e.g., vanadium content, nickel content), C/H ratio, or any combination thereof.

At 730, using the characterization (assay) data of the given crude oil (sample), and the data of the organometallic classes and subclasses and other hydrocarbon classes and subclasses, the computer system or processor 700 determines the organometallic classes and subclasses and other hydrocarbon classes and subclasses present in the given crude oil. The organometallic classes and subclasses can be selected, for example from the structural formulas represented in FIGS. 1A-B.

At 740, using the characterization (assay) data of the given crude oil, and physical and chemical property data for each segment type and segment number range, the computer system 50, 60 or processor 700 determines the segment types and segment number ranges bound to the organometallic classes and subclasses present in the given crude oil. Step 740 may utilize PC-SAFT to identify the segment types and segment number ranges.

At 750, the computer system 50,60 or processor 700 determines a relative ratio of each organometallic class and subclass to each other organometallic class and subclass that forms a chemical composition representative of the given crude oil (sample). The determined relative ratio and the determined respective organometallic class and subclass, segment type, and segment number range form a characterization of the metal content and the chemical composition of the given crude oil. In an example embodiment, the relative ratio can be determined by a probability distribution function for the organometallic class and subclass, the segment type, and segment number range. Identification of the scale and shape parameters of the probability distribution function can be used to determine the metal content and the chemical composition of the given crude oil.

Using the identified scale and shape parameters, step 750 estimates the metal content and the chemical composition of the given crude oil. Next, step 750 estimates the physical and chemical properties of the given crude oil as a function of the estimated metal content and the chemical composition. In particular, step 750 derives the estimation of the physical and chemical properties, for example, from the known physical and chemical properties for the organometallic classes and subclasses and other hydrocarbon classes and subclasses, segment types, and segment number ranges, as described above. Examples of physical properties that can be estimated include, for example, boiling point, density, viscosity, or any combination thereof. Examples of chemical properties that can be estimated include carbon content, hydrogen content, oxygen content, nitrogen content, sulfur content, vanadium content, nickel content, or any combination thereof.

In another example embodiment, step 750 determines the relative ratio of each organometallic class and subclass by matching the estimated physical and chemical properties of the given crude oil against certain crude oil characterization (assay) data in order to determine the relative ratio of each organometallic class and subclass in the given crude oil to each other organometallic class and subclass that form a chemical composition representative of the given crude oil.

At 760, the computer system 50, 60 or processor 700 compares the estimated physical and chemical properties of the determined chemical composition representative of the crude oil to the actual characterization (assay) data received from, for example, the FT-ICR-MS derived data of the given crude oil. If the estimated data and the characterization (assay) data are consistent to within a pre-prescribed tolerance, step 770 generates a display or graphical representation of the formed characterization of the chemical composition and the metal content. Step 770 provides the generated graphical representation/display as an output to the end user. If the estimated properties are not consistent at step 760, then the processor 700 repeats step 750 to determine (refine) the probability distribution function and relative ratios again until the estimated properties and the characterization (assay) data are consistent to within the pre-prescribed tolerance.

At 780, once the determined chemical composition and metal content are either displayed to the end user (at 770) or determined to be consistent with the characterization (assay) data at 760, the computer system 50,60 can represent (or model), at 780, the given crude oil using the characterized metal content and chemical composition of the given crude oil. This model, including the predicted physical and chemical properties of the given crude oil, at 780, can be used to plan, schedule, simulate, design, optimize, and/or control petroleum refining operations.

Figure 8B:
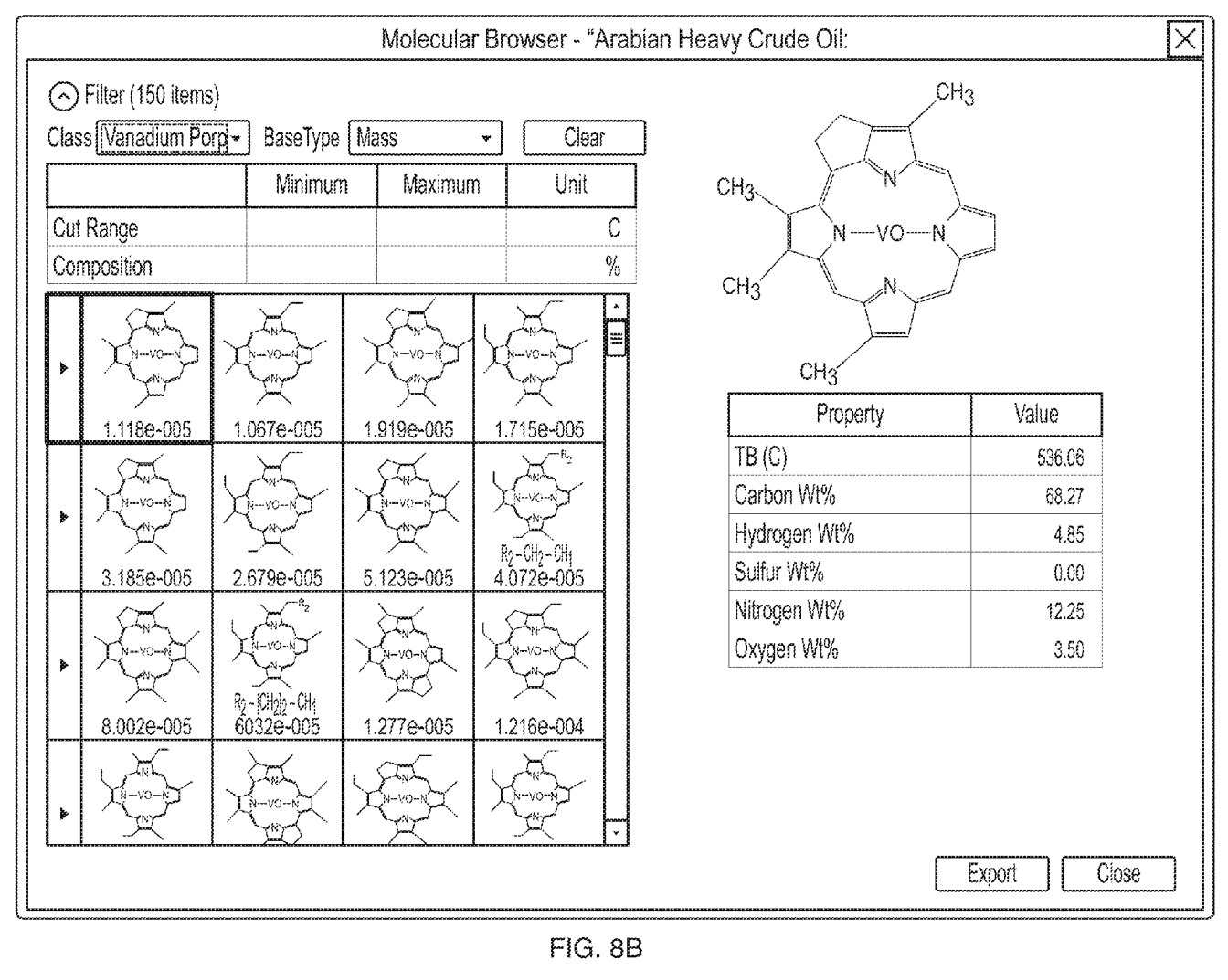

In an example embodiment, the present invention characterizes a chemical composition of crude oil, wherein the chemical composition comprises a metal and other hydrocarbon compounds. The resulting characterization is displayed, as output to an end-user, as the formed characterization of the metal content and the chemical composition of the given crude oil, as seen in FIGS. 8A and 8B. FIG. 8A displays obtained parameters for the gamma distribution function (see Eq. 1) for the segments of Nickel and Vanadium porphyrins classes. These parameters are used to determine the mass composition of Vanadium porphyrins compounds as shown in FIG. 8B. For this particular crude oil, 150 such compounds are identified.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

For example, computer methods and systems of the present invention describe and predict (by representing a characterization) metal content present in crude oil reactor feedstocks, and reactor products. Embodiments identify individual metal compounds classes, such as but not limited to nickel and vanadyl porphryins, present in crude oil and with such identification enable metal tracking and removal.

In one embodiment, the computer-based method is based on molecular-level representation of petroporphyrins and porphyrin-related compounds using assay data of crude oils. Porphyrin-related compounds comprise a porphyrin structure connected to other polycyclic aromatic hydrocarbon structures by methylene or sulfur linkages. The metal content characterization (molecular composition distribution in terms of model compounds of petroporphyrins and porphyrin-related classes) is used in crude oil processing models to track metal content through the distillation process and to predict make-up of reactor products.

What is claimed is:

1. A computer-implemented method of characterizing a chemical composition of crude oil, said method comprising:
   by a processor:
   a. providing physical and chemical property data for organometallic classes, segment types associated with the organometallic classes, and segment number ranges of the segment types;
   b. providing characterization data of a crude oil;
   c. determining at least one organometallic class and at least one organometallic subclass present in the crude oil based on (i) the provided physical and chemical property data for the organometallic classes and (ii) the provided characterization data of the crude oil;
   d. determining at least one segment type and at least one segment number range bound to the determined at least one organometallic class present in the crude oil based on (i) the provided physical and chemical property data for the segment types and the segment number ranges and (ii) the provided characterization data of the crude oil;
   e. determining a relative ratio between each of the at least one organometallic class that forms a chemical composition representative of the crude oil, such that the determined relative ratio, the determined at least one organometallic class, the determined at least one organometallic subclass, the determined at least one segment type, and the at least one segment number range form a characterization of the metal content and the chemical composition of the crude oil; and
   f. controlling refinery process operations using the formed characterization of the metal content and the chemical composition.

2. The method of claim 1, wherein the determined at least one segment type includes a methyl segment, a zero-branch methylene segment, a one-branch methylene segment, a two-branch methylene segment, a carbocyclic segment, a heterocyclic segment, an aryl segment, a heteroaryl segment, a sulfide segment, or any combination thereof.

3. The method of claim 1, wherein the determined least one organometallic class is a porphyrin compound comprising a metal.

4. The method of claim 3, wherein the metal is vanadium.

5. The method of claim 3, wherein the metal is nickel.

6. The method of claim 1, further comprising: estimating physical and chemical property values of the crude oil as a function of the determined at least one organometallic class, the determined at least one segment type, and the determined at least one segment number range.

7. The method of claim 1, wherein determining the at least one organometallic class, the at least one segment type, and the at least one segment number range includes identifying a probability distribution function for the at least one organometallic class, the at least one segment type, and the at least one segment number range, and wherein identifying of the probability distribution function includes identifying scale and shape parameters of the probability distribution function.

8. The method of claim 7, further comprising: estimating the metal content and the chemical composition of the crude oil as a function of the identified probability distribution functions and each determined relative ratio, and estimating physical and chemical properties of the crude oil as a function of the estimated metal content and the estimated chemical composition.

9. The method of claim 8, wherein the estimated physical properties of the crude oil include any one of: boiling point, density, viscosity, or any combination thereof.

10. The method of claim 8, wherein the estimated chemical properties of the crude oil include any one of carbon content, hydrogen content, oxygen content, nitrogen content, sulfur content, vanadium content, nickel content, or any combination thereof.

11. The method of claim 8, further comprising determining whether the formed characterization is representative of the crude oil by matching the estimated physical and chemical properties of the crude oil against the provided characterization data of the crude oil.

12. The method of claim 1, wherein the physical property data of the at least one organometallic class includes any one of boiling point, density, and viscosity, or any combination thereof.

13. The method of claim 1, wherein the chemical property data of the organometallic classes includes any one of carbon content, hydrogen content, oxygen content, nitrogen content, sulfur content, vanadium content, nickel content, or any combination thereof.

14. The method of claim 1, wherein the characterization data includes any one of boiling point, density, viscosity, or any combination thereof.

15. The method of claim 14, wherein the characterization data of the crude oil further includes any one of paraffinic content, naphthenic content, aromatic content, carbon content, hydrogen content, nitrogen content, oxygen content, sulfur content, vanadium content, nickel content, C/H ratio, or any combination thereof.

16. The method of claim 1, further comprising: predicting physical and chemical properties of the crude oil by representing the crude oil using the formed characterization of the metal content and the chemical composition of the crude oil.

17. The method of claim 16, further comprising: using at least one of the formed characterization of the chemical composition and the predicted physical and chemical properties to at least one of: plan, schedule, simulate, design, optimize, and control petroleum refining operations.

18. The method of claim 1, wherein the at least one segment number range is between 0 and 3 inclusive for aromatic side rings, between 0 and 3 inclusive for naphthenic side rings, and between 1 and 60 inclusive for side chain carbons.

19. The method of claim 1, wherein the at least one organometallic class is determined by the metal content in the provided physical and chemical property data of the organometallic classes.

20. A computer-based crude oil refinery process system comprising:
   a computer memory storing characterization data of a crude oil; and
   a processor coupled to the memory, the memory storing instructions that when executed by the processor cause the processor to:

produce a model representation of the crude oil including characterizing a metal content and a chemical composition of the crude oil by:
(a) providing physical and chemical property data for organometallic classes, segment types associated with the organometallic classes, and segment number ranges of the segment types;
(b) providing characterization data of the crude oil;
(c) determining at least one organometallic class and at least one organometallic subclass present in the crude oil based on (i) the provided physical and chemical property data for the organometallic classes and (ii) the provided characterization data;
(d) determining at least one segment type and at least one segment number range bound to the determined at least one organometallic class present in the crude oil based on (i) the provided physical and chemical property data for the segment types and the segment number ranges and (ii) the provided characterization data; and
(e) determining a relative ratio between each of the at least one organometallic class that forms a chemical composition representative of the crude oil, such that the determined relative ratio, the determined at least one organometallic class, the determined at least one organometallic subclass, the determined at least one segment type, and the determined at least one segment number range form a characterization of the metal content and the chemical composition of the crude oil; and
control refinery process operations using the formed characterization of the metal content and the chemical composition.

* * * * *

UNITED STATES PATENT AND TRADEMARK OFFICE
CERTIFICATE OF CORRECTION

PATENT NO. : 10,393,723 B2
APPLICATION NO. : 15/047347
DATED : August 27, 2019
INVENTOR(S) : Suphat Watanasiri, Shu Wang and Lili Yu It is certified that error appears in the above-identified patent and that said Letters Patent is hereby corrected as shown below:

On the Title Page

Item (63), delete "Continuation-in-part of application No. 13/740,095, filed on Jan. 11, 2013, now Pat. No. 9,934,367.".

Item (60), delete "Provisional application No. 61/644,792, filed on May 9, 2012, provisional application No. 61/586,268, filed on Jan. 13, 2012, provisional application No. 62/155,791, filed on May 1, 2015." and insert -- Provisional application No. 62/155,791, filed on May 1, 2015. --.

Signed and Sealed this
Twenty-fourth Day of December, 2019

Andrei Iancu
*Director of the United States Patent and Trademark Office*